United States Patent [19]

Riley

[11] Patent Number: 5,097,865
[45] Date of Patent: Mar. 24, 1992

[54] VALVED FLASH STERILIZATION CONTAINER

[75] Inventor: Edward D. Riley, Portland, Me.

[73] Assignee: Riley Medical, Inc., Auburn, Me.

[21] Appl. No.: 668,585

[22] Filed: Mar. 13, 1991

[51] Int. Cl.⁵ .............................................. F16K 15/06
[52] U.S. Cl. .................................. 137/529; 137/536; 422/112
[58] Field of Search ............... 137/494, 510, 469, 906, 137/529, 536, 543.15; 422/112

[56] References Cited

U.S. PATENT DOCUMENTS

| | | | |
|---|---|---|---|
| 2,618,290 | 11/1952 | Van Vliet | 157/536 X |
| 2,704,548 | 3/1955 | Ralston | 137/469 |
| 2,871,877 | 2/1959 | Work | 137/469 |
| 3,366,136 | 1/1968 | Burton | 137/529 X |
| 3,689,025 | 9/1972 | Kiser | 137/906 X |
| 4,664,142 | 5/1987 | Bertsch et al. | 137/510 X |
| 4,748,003 | 5/1988 | Riley | 137/493.7 X |

Primary Examiner—Stephen M. Hepperle
Attorney, Agent, or Firm—Cesari anrd McKenna

[57] ABSTRACT

A pressure responsive valve assembly for a sterilization container having a valve opening comprises a valve closure member for closing the opening and a fluid tight plenum chamber including a rigid wall and an opposite movable wall connected to the valve closure member for movement along a common axis therewith. A spring biases the movable wall and valve closure member away from the rigid wall of the plenum chamber. The movable wall has an area comparable to that of the valve closure member and the plenum chamber has a relatively small length-to-diameter ratio so that when the valve closure member is moved to open or close the valve, the resulting movement of the chamber movable wall changes the volume of the plenum chamber by less than 20%.

20 Claims, 2 Drawing Sheets

VALVED FLASH STERILIZATION CONTAINER

This invention relates to a container for flash sterilization. It relates more particularly to an improved valve for such a container.

BACKGROUND OF THE INVENTION

Articles such as medical instruments and the like are usually sterilized in an autoclave in which the articles are exposed to high pressure saturated steam for a relatively brief interval. Unless the articles are to be used immediately and in close proximity to the autoclave, it is desirable to sterilize the articles while they are inside a valved container as described, for example, in my U.S. Pat. No. 4,748,003.

During the sterilization process, the valves open under the influence of high pressure steam in the autoclave exposing the contents of the container to the hot steam. At the end of the sterilization cycle, when the pressure in the autoclave outside the container is returned to normal, i.e. atmospheric pressure, the valves close so that when the container is removed from the autoclave, the now sterilized articles are maintained in a completely sealed sterile environment until they are needed.

The sterilization container described in the above patent has pressure actuated valves in the top and bottom walls of the sterilization container. Each valve has a large valve opening and a closure therefor, the latter being supported by a bellows capsule mounted inside the container. A return spring mechanism normally maintains the valve closure in its closed position. However, when the pressure outside the container exceeds that within the container by a few pounds per square inch, the force on the valve closure exceeds that exerted by the return spring with the result that the valve closure opens sufficiently to allow high pressure steam to enter the container. That steam collapses the bellows which thereupon moves the valve closure to its fully open position. Both valves being open, high pressure steam can sweep through the container and sterilize the articles therein.

When the pressure inside the autoclave returns to normal after completion of the sterilization cycle, the return spring moves the valve closure of each valve to its closed position thereby sealing the container. As also described in that patent, pressure equalization occurs through a special filter member mounted in the container wall so that a sterile environment at ambient pressure is maintained in the container until the container is opened to remove the articles therefrom.

While the valve described in the above patent operates satisfactorily, it does have certain drawbacks. First and foremost, the bellows capsule has a relatively small diameter in relation to the valve opening and a large length-to-diameter ratio, e.g. 1.3 in./1 in. = 1.3. This means that when the valve member starts to open in response to a given pressure differential outside and inside the container and the bellows is collapsed lengthwise, there is a relatively large reduction in the volume of the bellows, i.e. in excess of 20%, and a correspondingly large increase in gas pressure inside the bellows which resists further opening of the valve member.

To avoid this problem, the bellows capsule in the prior value has to be evacuated. This necessitates the use of an elaborate return spring mechanism in order to overcome the increased back pressure and close the valve. Also, the requirement for a bellows that must be evacuated makes the valve somewhat more difficult and expensive to manufacture. In addition, sometimes a small leak may develop in the bellows so that air enters the bellows. Resultantly, during the next sterilization cycle, when the valve member begins to open, that air will be compressed, effectively increasing the spring constant of the bellows so that the valve member does not open as much for a given pressure differential outside and inside the container.

SUMMARY OF THE INVENTION

Accordingly, it is an object of the invention to provide a sterilization container whose valves are rugged, reliable and easy to service.

Another object of the invention is to provide a sterilization container incorporating valves which can be opened by a minimum pressure differential outside and inside the container.

Another object of the invention is to provide a valve for a sterilization container which does not include any bellows or other parts that have to be maintained at a pressure above or below atmospheric.

A further object of the invention is to provide a valve of this general type which has a large valve opening and which opens consistently and quickly in response to a selected small pressure differential across the valve.

Other objects will, in part, appear hereinafter. The invention accordingly comprises the features of construction, combination of elements and arrangement of parts which will be exemplified in the following detailed description, and the scope of the invention will be indicated in the claims.

Briefly, my sterilization container has large top and bottom openings that are closed by pressure-sensitive valves. The valves seal the openings at normal, i.e. atmospheric, pressure. When the container is placed in an autoclave and steam is introduced into the autoclave, the increase in outside pressure causes the valves to open, so that high pressure saturated steam can enter and sweep through the container, flash sterilizing the container contents in the process. When the pressure in the autoclave is reduced at the end of the sterilization cycle, the valves close thereby sealing the openings so that the container contents will be maintained in a sterile condition until they can be removed from the container. Each valve in the present container thus performs the same function as those described in the aforesaid patent.

The new valve differs, however, in that it incorporates a relatively large volume plenum chamber having a movable wall in the form of a special, large diameter, flexible, resilient conical diaphragm which supports the valve closure member and which helps to maintain that member in its closed position when there is no pressure differential across the valve. The diaphragm is comparable in area to the areas of the valve opening and closure member and the plenum has an effective length-to-diameter ratio, which is quite small, i.e. appreciably less than 1.

Resultantly, even when the plenum is filled with air at atmospheric pressure, when the diaphragm is deflected as the valve closure member opens, there is only a relatively small reduction in the total volume of the plenum. Indeed, the volume reduction is insufficient to increase the pressure inside the plenum enough to resist or appreciably retard further opening of the valve. In other words, in response to a very small increase in outside pressure, the valve member opens sufficiently to expose the large area diaphragm to the high pressure steam. Absent any appreciable opposing force due to increasing back pressure in the plenum, the conical diaphragm inverts and immediately moves the valve member to its fully open position, allowing high pressure steam to burst through the valve opening.

When the pressure outside the container returns to normal, i.e. atmospheric, a relatively small return spring suffices to return the diaphragm and valve member to their original positions, thereby closing the valve.

The valve is composed of a relatively few components which are relatively easy and inexpensive to make in quantity. Furthermore, these components can be assembled quite easily so that assembly and maintenance costs are kept to a minimum. When installed in a sterilization container, the valve provides a very effective and reliable means for exposing the contents of the container to quick bursts of high pressure saturated steam from an autoclave during a sterilization cycle and for providing an effective seal following sterilization so that the interior of the container is maintained in a septic condition.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENT

Figure 1:
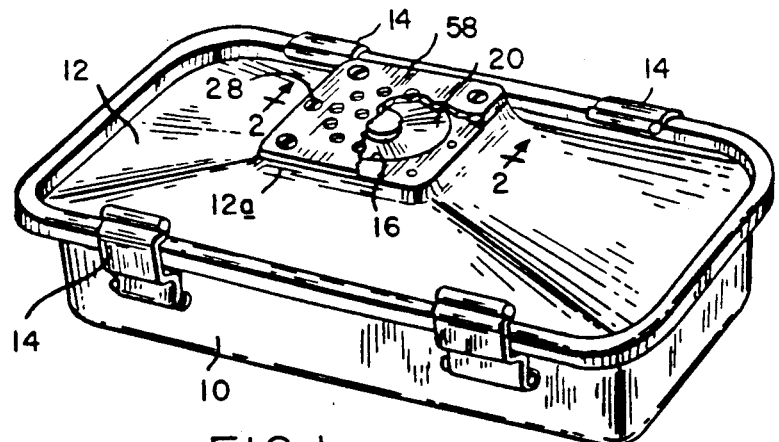
FIG. 1 is an isometric view with parts cut away showing a valved sterilization container according to this invention.
Figure 2:
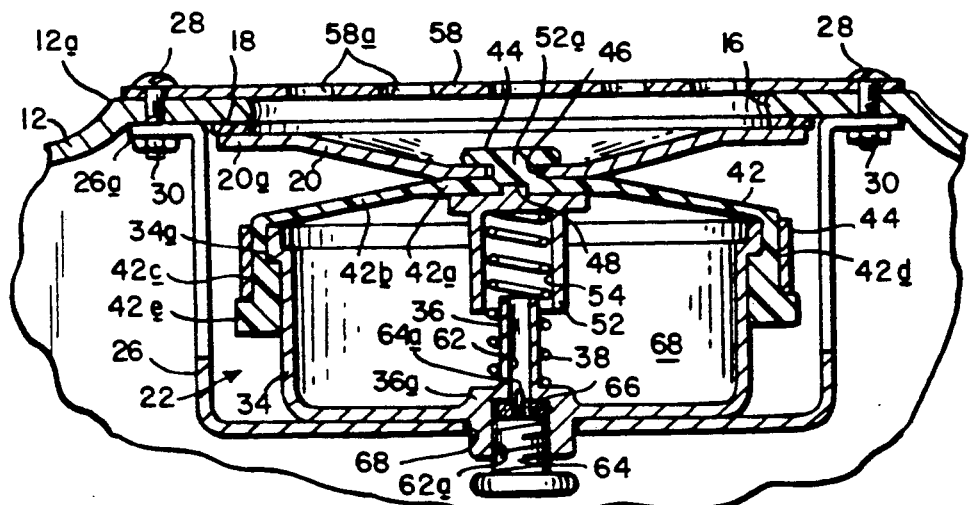
FIG. 2 is a sectional view on a much larger scale showing in detail a pressure actuated valve in the FIG. 1 container, with the valve closure member being in its closed position.

Referring to FIGS. 1 and 2 of the drawings, a flash sterilization container incorporating the invention comprises a bowl 10 and a cover 12 for closing the top of the bowl. A suitable seal or gasket (not shown) is provided around the edge of the bowl and/or the edge of the cove to provide a hermetic seal around the container when the cover is secured to the bowl by means of the locking clips 14.

Cover 12 has a central mesa 12a provided with a relatively large diameter circular opening 16. A gasket 18 extending around the perimeter of opening 16 at the underside of cover 12 functions as a valve seat for a valve closure member 20. Member 20 is shaped, more or less, like a cymbal and it has a flat peripheral margin 26a which is arranged to seat against gasket 18. The valve member has a diameter which is somewhat larger than that of opening 16, 3.5 inches in this example, so that the member can effectively close the opening.

Valve member 20 is part of a pressure responsive valve assembly shown generally at 22 which is supported inside cover 12 opposite opening 16 by a generally U-shaped bracket 26. Bracket 26 engages under the assembly and the ends of the bracket legs are turned outward to form flanges 26a. The bracket is suitably secured to cover 12 at opposite sides of opening 16 such as by threaded fasteners 28 which extend through registering openings in the cover and flanges and are threaded into nuts 30.

Figure 4:
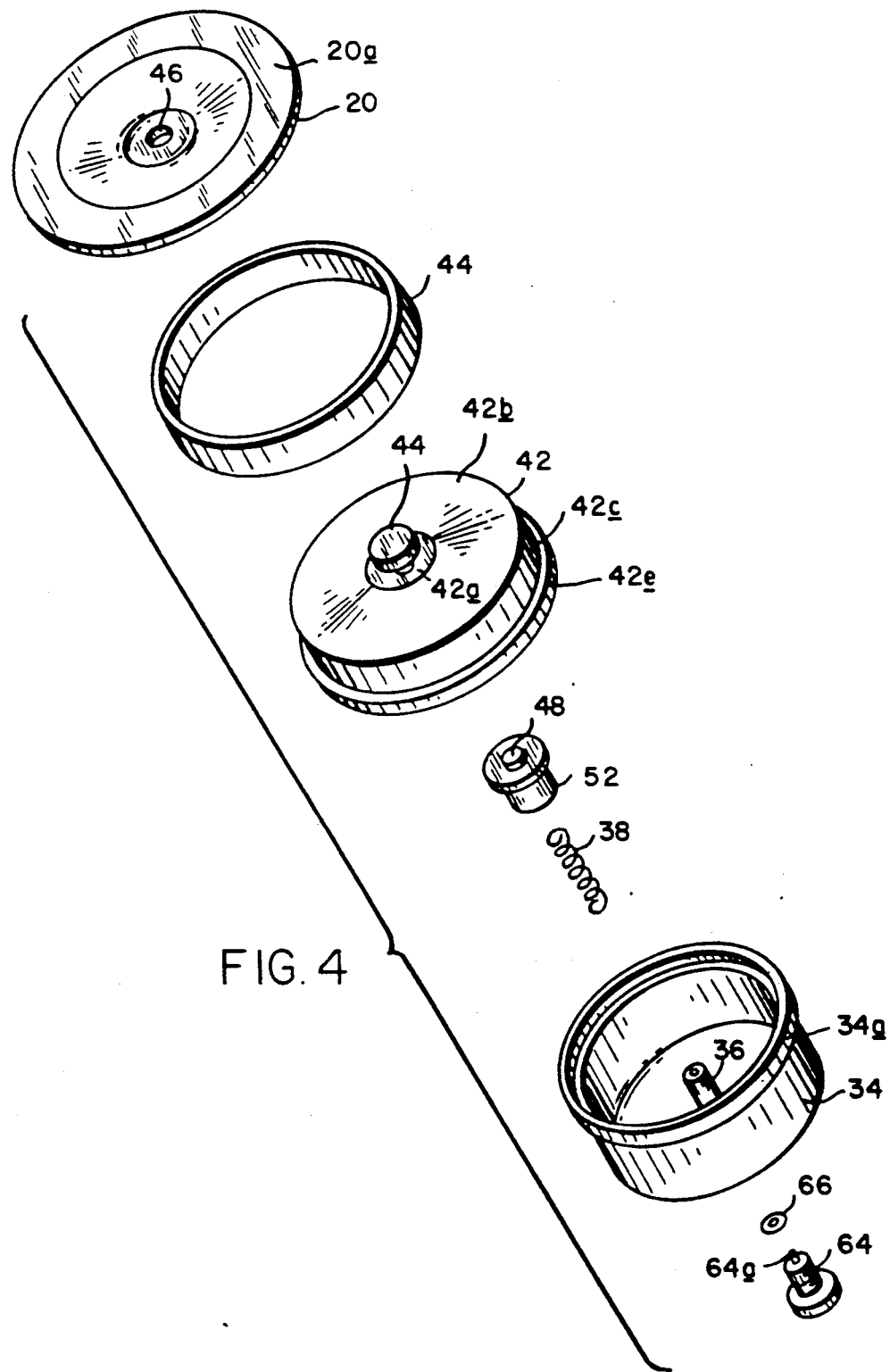
FIG. 4 is an exploded isometric view showing the various components of the container valve.

Referring to FIGS. 2 and 4 of the drawings, valve assembly 22 comprises a rigid cup 34 which is in the order of 3 inches in diameter and 1 inch deep. The cup is formed with an enlargement 34a that extends all around the cup at the rim thereof. Also, a central pedestal 36 projects up from a central foundation boss 36a at the bottom wall of cup 34 to locate an upstanding coil spring 38 within the cup.

The open top of cup 34 is closed by a movable wall in the form of a flexible, resilient diaphragm 42. Preferably, the diaphragm is cupped toward valve member 20. The illustrated diaphragm has a relatively flat central area 42a and a relatively large conical portion 42b which extends from area 42a to a depending skirt 42c which tightly encircles the upper portion of the cup 34 side wall, including the enlargement 34a.

A cylindrical channel 42d is formed in the inside surface of skirt 42c. This channel interfits with the enlargement 34a at the rim of cup 34 so that when the diaphragm is engaged over the cup as shown in FIG. 2, a fluid tight seal is established between the diaphragm and the cup all around the rim of the cup. Preferably, a non-extensible ring 44 is slid over the diaphragm 42 so that it tightly encircles the diaphragm skirt 42c to lock the diaphragm to the side wall of cup 34. A peripheral flange 42e at the bottom of the diaphragm skirt 42c provides a positive seat for the ring 44.

Still referring to FIGS. 2 and 4, diaphragm 42 is formed with an integral raised deformable button 44 at its central area 42a. This button is received in a central opening 46 in valve member 20 to flexibly secure that member to the diaphragm. If it becomes necessary to separate member 20 from the diaphragm, this can be done by deforming the button and forcing it back through opening 46.

A locating hole 48 is formed in the underside of the diaphragm portion 42a at the center thereof for locating a depending post 52. Post 52 has an end boss 52a which seats in hole 48 to center the post on the diaphragm central axis. A passage 54 extending in from the opposite or lower end of post 52 receives the upper end of spring 38 so that the post can telescope onto pedestal 36 thus capturing the spring. Spring 38 biases post 52, diaphragm portion 42a and valve closure member 20 upwards so that the edge margin 20a of the valve member is urged to seat against the gasket 18 encircling valve opening 16, as shown in FIG. 2.

In order to prevent objects from entering valve opening 16 and possibly interfering with the proper operation of the valve, a perforated plate 58 is secured to the top of mesa 12a by fasteners 28 and nuts 30 or by other suitable means. The perforations 58a in plate 58 should be relatively large and numerous enough so that air and steam can flow freely through the plate.

Preferably for reasons to be discussed later, the pedestal 33, including its foundation boss 36a, is provided with an axial passage 62 as shown in FIGS. 2 and 4. The outer or lower end segment of that passage in boss 36a is counterbored and threaded at 62a to receive a thumb screw 64. An O-ring 66 encircles the reduced diameter inner end 64a of the thumb screw 64 so that when the thumb screw is turned down into counterbore 62a, a fluid-tight seal is provided at the bottom of the counterbore.

When valve assembly 22 is assembled as shown in FIG. 2, it defines a large volume plenum 68 between cup 34 and diaphragm 42, having a length-to-diameter ratio appreciably less than 1, i.e. 1 in./3 in.=0.33 in the illustrated valve assembly. When the diaphragm is properly seated on the cup and the thumb screw 64 is tightened, the plenum is essentially hermetically sealed. Normally, when a gas, i.e. air, within the plenum is near ambient temperature (i.e. 50° to 100° F.), the pressure within the plenum is approximately atmospheric pressure. This condition can be assured simply by loosening the thumb screw 64 and venting the plenum to room air.

With atmospheric pressure in the plenum chamber 68, the valve closure member 20 is urged against its seat at gasket 18 by the spring 38 which is chosen to provide a force in the order of 1 to 3 lbs. when the valve member 20 is in its closed position and there is no pressure differential across diaphragm 42. The resilient diaphragm itself may exert an additional small closing force due to some deflection of its conical portion 42b.

Figure 3:
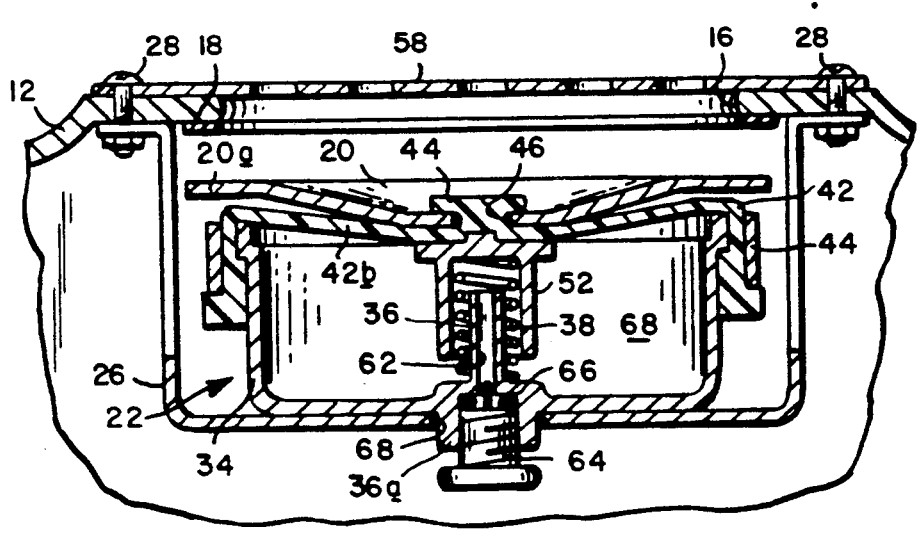
FIG. 3 is a similar view of the valve, with the valve member in its open position.

When the container is placed in an autoclave and saturated steam at a relatively high pressure, (e.g. 30 psi), is introduced into the autoclave, the pressure differential across valve member 20 will cause the valve to open slightly. Resultantly, diaphragm 42 becomes exposed to the full pressure of that steam which is substantially greater than the pressure inside plenum 68 which, as noted previously, is normally atmospheric pressure. The pressure differential across diaphragm 42 causes the diaphragm to immediately invert which motion drives the valve member 20 to its fully open position shown in FIG. 3. The opening force is due not only to the aforesaid pressure differential on the diaphragm 42, but also the inverting force arising because of the shape of the conical diaphragm itself.

In the illustrated valve embodiment, the valve member 20, when opening, may move a distance in the order of 0.4 inch. However, due to the large diameter of the diaphragm 42, i.e. about 3 inches, and the small length-to-diameter ratio of plenum 68 as a whole, i.e. about 0.33, this results in a volume decrease of the plenum 68 of less than 20%, i.e. only about 17% in the illustrated valve. This minimizing of the change in the volume of the plenum chamber minimizes the change in the plenum pressure and thus in the external pressure required to open the valve. Typically, an external pressure increase in the order of only 3 to 4 psi is needed to cause valve member 20 to be moved to its fully open position shown in FIG. 3.

After prolonged operation of valve assembly 22, after it has been subjected to repeated sterilization cycles, the gas pressure in plenum chamber 68 may become lower than atmospheric pressure due to a slight porosity of the diaphragm 42 material. If the pressure within the plenum becomes sufficiently low, it may inhibit diaphragm 42 from returning to its fully extended position shown in FIG. 2. Resultantly, following a sterilization cycle, the valve closure member 20 may not reach its fully closed position against gasket 18 so that the sterile environment inside the container may be compromised. To avoid this potential problem, at recommended intervals, the user may loosen the thumb screw 64 to vent plenum chamber 68 to room air.

A similar procedure may be followed if the container undergoes several sterilization cycles in a short period of time. In this event, the temperature of the air in the plenum may be increased sufficiently to raise the air pressure appreciably above atmospheric pressure when the valve member 20 is in its closed position. This will increase the amount of external pressure required to open the valve. Venting the plenum from time to time by momentarily loosening thumb screw 64 will avoid this potential problem.

As shown in FIGS. 2 and 4, the components of valve assembly 22 may be relatively simple stamped metal or molded plastic parts which can be made easily in quantity at relatively low cost. The cup 34, ring 44, post 52 and thumb screw 64 may be molded of a suitable relatively rigid, heat-resistant, medical grade plastic material. The valve member 20 may be stamped of metal, e.g. stainless steel, or the aforesaid plastic material, and the diaphragm 42 may be molded of a suitable flexible, resilient heat-resistant, medical grade, plastic material such as silicone rubber. The remaining parts of the assembly, such as spring 38 and gaskets 18 and 66, are more or less standard off-the-shelf items.

To assemble the various components of the valve, spring 38 is placed on the cup pedestal 36 and post 52 is engaged over the spring and pedestal. Next, the diagram 42 is engaged over cup 34 so that the post boss 52a engages in the locating hole 48 of the diaphragm and the diaphragm skirt 42c is forced down around the side wall of the cup until the skirt channel 42d interlocks with the cup enlargement 34a. Then, the locking ring 44 is slipped over the upper end of the diaphragm and engaged around skirt 42c so that it seats on the diaphragm flange 42e. Finally, the valve closure member 20 is secured to the diaphragm by inserting the diaphragm button 44 through the central opening 46 in member 20. Then, after screwing thumb screw 64 into counterbore 62a of cup 34, bracket 26 is engaged under valve assembly 22. A clearance hole 68 is provided in the bracket to accommodate the boss 36a and to fix the relative positions of the cup 34 and bracket. Finally, the bracket is secured to cover 12 by means of the threaded fasteners 28 and nuts 30 or by other suitable means.

If it becomes necessary to clean, repair or replace one or another of the assembly components, this can be done quickly and easily by reversing the above procedure. Therefore, such repair and maintenance should cause only minimal downtime of the associated container.

It will thus be seen that the objects set forth above, among those made apparent from the preceding description, are efficiently attained, and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described.

I claim:

1. In a valved sterilization container of the type including a relatively large valve opening in a wall of the container and a pressure responsive valve assembly having a valve closure member with a central axis, the improvement wherein the valve assembly comprises
a fluid tight plenum chamber having a movable wall facing the valve closure member, said plenum chamber having an area perpendicular to said axis which is comparable to the area of the valve closure member, a length-to-diameter ratio appreciably less than 1 and an internal pressure not appreciably above the pressure outside the chamber;

means for connecting together the valve closure member and chamber movable wall so that they are movable along said axis, said valve closure member being movable between a closed position in which said valve closure member closes said opening and a fully open position in which the valve closure member does not occlude said opening, and biasing means for urging the valve closure member toward said closed position, whereby movements of the valve closure member between its closed and fully open positions in response to pressure changes across the valve, changes the volume of the plenum chamber by less than 20%.

2. The container defined in claim 1 wherein the plenum chamber is generally cylindrical and the valve closure member and valve opening are circular.

3. The container defined in claim 1 wherein said movable plenum chamber wall comprises a flexible diaphragm.

4. The container defined in claim 3 wherein said diaphragm is resiliently cupped toward said valve closure member.

5. The container defined in claim 1 and further including means for selectively venting the plenum chamber to the atmosphere.

6. The container defined in claim 5 wherein the venting means comprise
means defining an opening into the plenum chamber, and
releasable closure means for closing said opening.

7. A pressure responsive valve assembly for a sterilization container of the type having a valve opening, said valve assembly comprising
a generally cylindrical, fluid tight plenum chamber, said chamber having a rigid wall, a discoid movable wall spaced opposite the rigid wall, a length-to-diameter ratio appreciably less than 1 and an internal pressure that is not appreciably above the pressure outside the chamber;
a discoid valve closure member for closing said opening, said closure member having a diameter similar to that of said movable wall;
means for connecting together the valve closure member and movable wall so that the valve closure member and movable wall are movable along a common axis, and
biasing means for urging said valve member and movable wall along said axis away from the rigid wall of the plenum chamber.

8. The valve assembly defined in claim 7 wherein said movable wall is a flexible diaphragm.

9. The valve assembly defined in claim 8 wherein said diaphragm is resiliently cupped toward said valve closure member and inverts when moved toward the rigid wall of the plenum chamber.

10. The valve assembly defined in claim 9 wherein said diaphragm includes a conical segment.

11. The valve assembly defined in claim 9 wherein said valve closure member is cupped toward said diaphragm so that it nests in said diaphragm when the diaphragm inverts.

12. The valve assembly defined in claim 7 and further including means for selectively venting the plenum chamber to the atmosphere.

13. The valve assembly defined in claim 7 wherein said plenum chamber comprises a rigid, generally cylindrical cup whose bottom wall constitutes said rigid wall and having a rim, and
a flexible resilient diaphragm constituting said movable wall, said diaphragm having a peripheral skirt which snugly engages around said rim to provide a fluid tight seal between the cup and the diaphragm.

14. The valve assembly defined in claim 13 and further including plenum chamber venting means mounted in a wall of said cup.

15. The valve assembly defined in claim 13 wherein the area of the diaphragm is similar to that of the valve closure member.

16. The valve assembly defined in claim 7 wherein the biasing means comprise a spring compressed between the rigid and movable walls of the plenum chamber.

17. A valved sterilization container of the type including a relatively large valve opening in a wall of the container and a pressure-responsive valve assembly having a valve closure member with a central axis, the improvement wherein the valve assembly comprises;
a fluid-tight plenum chamber having a movable wall facing the valve member in the form of a flexible, conical diaphram which is resiliently cupped toward said valve closure member and which inverts when said valve closure member is moved to its fully opened position, said plenum chamber having an area of perpendicular to said axis which is comparable to the area of the valve closure member and a length-to-diameter ratio appreciably less than 1;
means for connecting together the valve closure member and diaphragm so that they are movable along said axis, said valve closure member being movable between a closed position in which said valve closure member closes said opening and a fully open position in which the valve closure member does not occlude said opening, and
biasing means for urging the valve closure member toward said closed position, whereby movements of the valve closure member between its closed and fully opened positions in response to pressure changes across the valve change the volume of the plenum chamber by less than 20%.

18. The container defined in claim 17 wherein said valve closure member is cupped in the opposite sense from the diaphragm so that it nests in the diaphragm when in its fully open position.

19. A pressure responsive valve assembly for a sterilization containder having a valve opening, said valve assembly comprising
a valve closure member for closing said opening;
a generally cylindrical, fluid-tight plenum chamber having a length-to-diameter ratio appreciably less than 1, said chamber including
a rigid, generally cylindrical cup having a bottom wall and a rim, and
a flexible resilient diaphram spaced opposite said bottom wall and having a peripheral skirt which snugly engages around said rim to provide a fluid-tight seal between the cup and the diaphram,
means for connecting together the valve closure member and diaphram so that the valve closure member and diaphram are movable along a common axis;

biasing means for urging said valve member and diaphram along said axis away from said cup bottom wall, and a locking ring snugly engaged around said skirt.

20. A pressure-responsive valve assembly for a sterilization container having a valve opening, said valve assembly comprising a valve closure member for closing said opening;

a generally cylindrical, fluid-tight plenum chamber having a length-to-diameter ratio appreciably less than 1, said chamber including a rigid, generally cylindrical cup having a bottom wall and a rim, and a flexible resilient diaphram spaced opposite said bottom wall and having a peripheral skirt which snugly engages around said rim to provide a fluid-tight seal between the cup and the diaphram, means for connecting together the valve closure member and diaphram so that the valve closure member and diaphram are movable along a common axis, said connecting means including an integral raised projection at the center of the diaphram and an opening at the center of the valve closure member which interfits with said projection, and biasing means for urging said valve closure member and diaphram along said axis away from said cup bottom wall.

* * * * *